(12) United States Patent
Sanso

(10) Patent No.: US 8,860,060 B1
(45) Date of Patent: Oct. 14, 2014

(54) LIGHT EMITTING DIODE INTEGRATED CABLE AND HEAT SINK

(71) Applicant: David Sanso, Golden, CO (US)

(72) Inventor: David Sanso, Golden, CO (US)

(*) Notice: Subject to any disclaimer, the term of this patent is extended or adjusted under 35 U.S.C. 154(b) by 68 days.

(21) Appl. No.: 13/714,382

(22) Filed: Dec. 13, 2012

Related U.S. Application Data

(60) Provisional application No. 61/570,663, filed on Dec. 14, 2011, provisional application No. 61/583,273, filed on Jan. 5, 2012.

(51) Int. Cl.
| | |
|---|---|
| *H01L 33/48* | (2010.01) |
| *H01L 33/58* | (2010.01) |
| *H01L 23/48* | (2006.01) |
| *A61B 1/06* | (2006.01) |
| *F21V 8/00* | (2006.01) |
| *H01L 23/49* | (2006.01) |
| *A61B 1/07* | (2006.01) |

(52) U.S. Cl.
CPC .............. *H01L 33/48* (2013.01); *H01L 33/58* (2013.01); *H01L 23/48* (2013.01); *A61B 1/0684* (2013.01); *G02B 6/0005* (2013.01); *H01L 23/49* (2013.01); *A61B 1/07* (2013.01); *G02B 6/0006* (2013.01)

USPC .............. 257/98; 362/581; 362/554; 385/54; 385/55; 385/58; 385/70; 385/76; 385/77; 385/86; 385/88; 385/115

(58) Field of Classification Search
USPC ........... 257/98; 362/581, 554; 385/54, 55, 58, 385/70, 76, 77, 86, 88, 115
See application file for complete search history.

(56) References Cited

U.S. PATENT DOCUMENTS

| | | | |
|---|---|---|---|
| 5,293,437 A * | 3/1994 | Nixon | 385/115 |
| 6,290,382 B1 * | 9/2001 | Bourn et al. | 362/554 |
| 6,513,962 B1 * | 2/2003 | Mayshack et al. | 362/583 |
| 6,595,674 B1 * | 7/2003 | Yoneda | 362/555 |
| 7,204,629 B2 * | 4/2007 | Pipo et al. | 362/559 |
| 2002/0159725 A1 * | 10/2002 | Bucklen | 385/101 |
| 2003/0231843 A1 * | 12/2003 | Colombo et al. | 385/115 |
| 2006/0041192 A1 * | 2/2006 | Klootz | 600/178 |
| 2006/0171693 A1 * | 8/2006 | Todd et al. | 396/17 |
| 2006/0173245 A1 * | 8/2006 | Todd et al. | 600/178 |
| 2007/0100211 A1 * | 5/2007 | Selover et al. | 600/199 |
| 2009/0040783 A1 * | 2/2009 | Krupa et al. | 362/555 |
| 2011/0021882 A1 * | 1/2011 | Selover et al. | 600/245 |
| 2011/0200959 A1 * | 8/2011 | Rizoiu et al. | 433/29 |

* cited by examiner

*Primary Examiner* — Long K Tran
*Assistant Examiner* — Jordan Klein
(74) *Attorney, Agent, or Firm* — Luis Figarella

(57) ABSTRACT

A high output light emitting diode (LED) based lighting module includes a plurality of LEDs support structures mounted on one or more electrical transfer structures, each said LED support structured securely holding a fiber bundle so that it mates to an LED so that each fiber bundle slightly overlaps the active area of its respective LED.

4 Claims, 3 Drawing Sheets

LIGHT EMITTING DIODE INTEGRATED CABLE AND HEAT SINK

CROSS-REFERENCE TO RELATED APPLICATIONS

This application claims priority to U.S. provisional patent application Ser. No. 61/570,663 titled "Light Emitting Diode Cable" filed on Dec. 14, 2011, Ser. No. 61/583,273 titled "Connector LED Heatsink" filed on Jan. 5, 2012, and Ser. No. 13/711,073 "Light Emitting Diode Cable and Heat Sink", filed on Dec. 11, 2012 the disclosure of all of the above herein incorporated by reference in their entirety.

PATENTS CITED

The following documents and references are incorporated by reference in their entirety, Savage, Jr., (U.S. Pat. No. 5,548,676), Wehner (U.S. Pat. No. 7,086,765), Ruffin (U.S. Pat. No. 7,182,496), Gingrich, III et al (U.S. Pat. No. 7,942,563), Simon et al (U.S. Pat. No. 8,256,924) and Huang (U.S. Pat. Appl. No. 2012/0194071).

FIELD OF THE INVENTION

The present invention relates generally to the field of light emitting diodes and of efficient ways to remove the heat generated by their operation. More specifically, the present invention is directed to a lighting device that allows for the use of multiple LEDs to be efficiently coupled with a light fiber bundle or cable in order to create high output lighting and efficiently removes the heat generated by these LEDs while maintaining a good optical coupling.

DESCRIPTION OF THE RELATED ART

Light emitting diodes (LEDs) are well known solid state light sources. LEDs have many advantages over traditional lighting sources such as incandescent bulbs and Compact Fluorescent bulbs (CFLs), as they are cheaper to produce, more robust and are more efficient in their use of power, typically requiring less power to generate the same amount of light. Because they are solid state devices, they are especially desirable as they emit light with high power efficiency over specific and customizable colors of the spectrum. A major problem of LEDs is that they are not focused light sources and suffer from relatively low light output. These shortcomings prevent application of LEDs in uses where high light intensity is desired.

There are many commercial applications requiring high light output, in particular in medical applications, where the above advantages are desired. For example, there is a great demand for LED light sources to replace the traditional halogen and other incandescent sources that are used in conjunction with optical fibers to deliver illumination within a body cavity.

When using LED/LED's to illuminate an optical fiber, the light output through the fiber drops off 5% per foot. Given a standard 8 Ft cable the LED light drops off by 30% from the LED to the end of the fiber. The closer the LED can be placed to the end of the fiber, the more efficient the overall system will be. A major problem when placing the LED at the end or close to the end of the fiber is the concentration of heat next to the camera head or the user. A few watts of heat can cause discomfort or affect the performance of the camera. While each LED by itself dissipates a small amount of heat, putting them in a small concentrated space can cause significant heat.

Of course, in any of these applications, there is a need to remove heat. Removing the heat from an LED array while maintaining good optical coupling in a removable system can be a challenge. In a camera system where the surgeon has to hold the camera in their hand, it would be uncomfortable to include the LEDs in the camera head due to the heat generated by the LEDs and their associated power electronics.

While the LEDs are an efficient form of generating light, there is still a fair amount of heat generated by an array of LEDs. Given the small active area of the LED and the precision at which they must be aligned, placing the LEDs in an enclosure and removing the heat from the enclosure will prohibit repeatable optical coupling between the light carrying fiber and the LEDs causing demised light output.

Thus, there is a need for an LED based device which provides sufficient light intensity for high lighting applications while at the same time efficiently removing the heat generated. There is a further need for an LED based device which allows light output to be focused and directed into the fiber optic assembly so that it allows for high light output from the end of an optic fiber. Finally, there is a pressing need for bringing said light source as close to the emitting part of the light fiber, in order to maximize the light output of these.

SUMMARY OF THE INVENTION

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention.

In one aspect the invention is about a high output light emitting diode (LED) based lighting module, comprising a light fiber cable formed by two or more light fiber bundles, an LED cylindrical housing containing a plurality of LED support structures, separated by some distance, thermally and electrically connected to one or more electrical and heat transfer structures, each said LED support structure mounting one or more LEDs and securely holding a light fiber bundle end against the light emitting portion of an LED so that said light fiber bundle end slightly overlaps the active area of said LED, and said LED cylindrical housing containing a portion of said light fiber cable as well as one or more electrical connectors interfacing to a detachable power source.

In another aspect, the invention further comprises a removable interface module, said removable interface module having one or more electrical connectors for coupling with said one or more LED cylindrical housing electrical connectors and one or more heat transfer and electrical connectors suitable for coupling with a base station, and a base station, said base station having one or more base-station electrical and heat connectors for coupling with said one or more removable interface module heat transfer and electrical connectors.

Other features and advantages of the present invention will become apparent upon examining the following detailed description of an embodiment thereof, taken in conjunction with the attached drawings.

The above-described and other features will be appreciated and understood by those skilled in the art from the following detailed description, drawings, and appended claims.

DETAILED DESCRIPTION OF THE PREFERRED EMBODIMENT

To provide an overall understanding of the invention, certain illustrative embodiments and examples will now be described. However, it will be understood by one of ordinary skill in the art that the same or equivalent functions and sequences may be accomplished by different embodiments that are also intended to be encompassed within the spirit and scope of the disclosure. The compositions, apparatuses, systems and/or methods described herein may be adapted and modified as is appropriate for the application being addressed and that those described herein may be employed in other suitable applications, and that such other additions and modifications will not depart from the scope hereof.

All references, including any patents or patent applications cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents form part of the common general knowledge in the art. It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Figure 1:
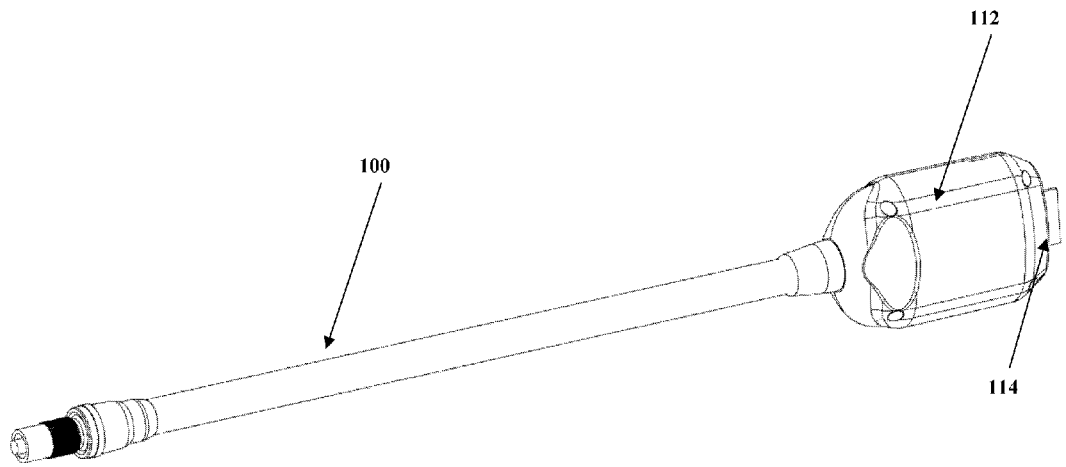
FIGS. 1-6 show various illustrations of a multi-LED light source utilizing multi-LEDs and other components, according to an exemplary embodiment of the invention.
Figure 2:
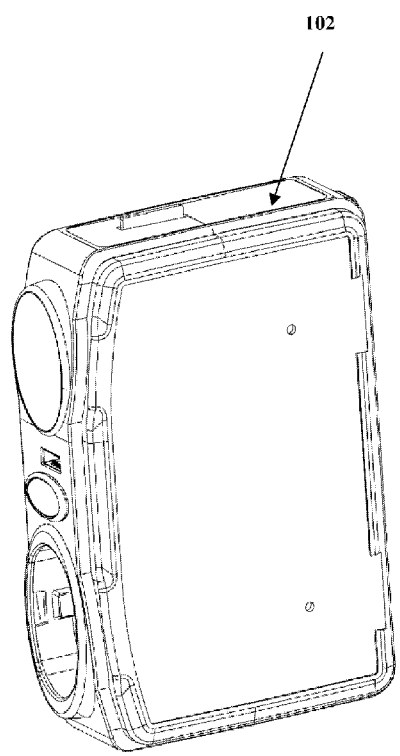
Figure 3:
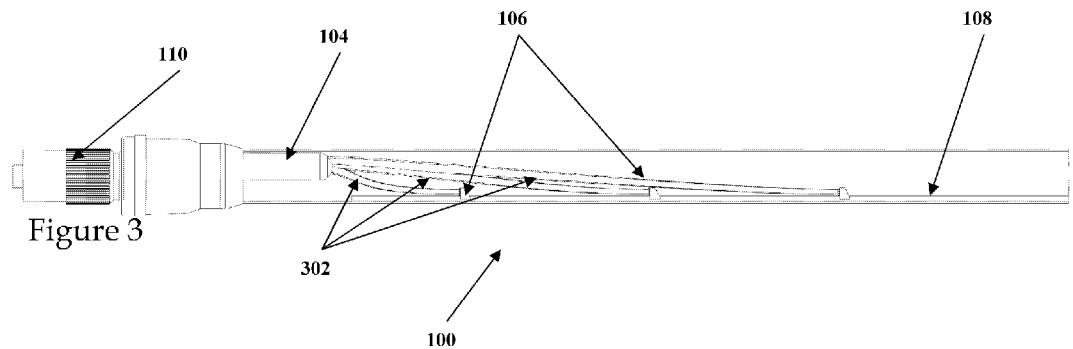
Figure 4:
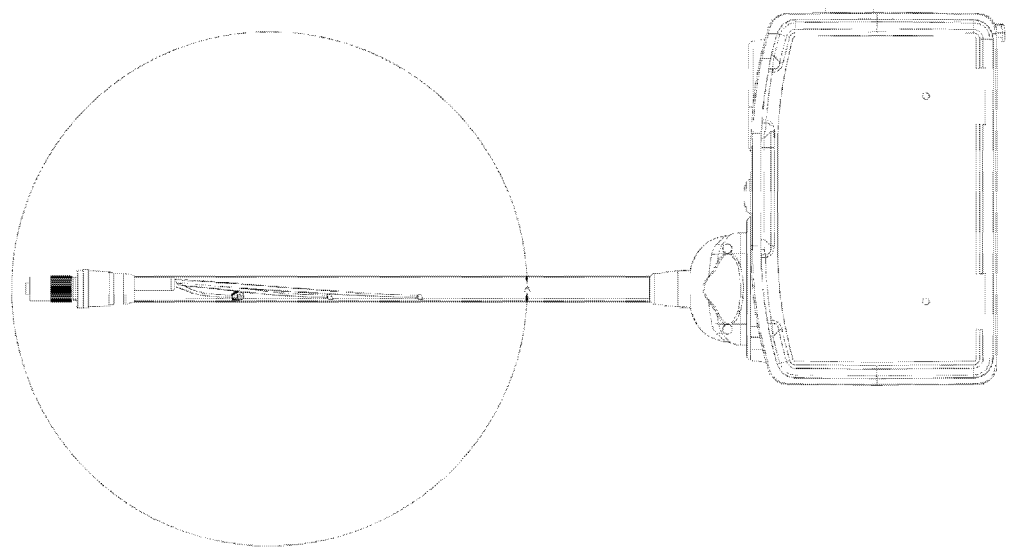
Figure 5:
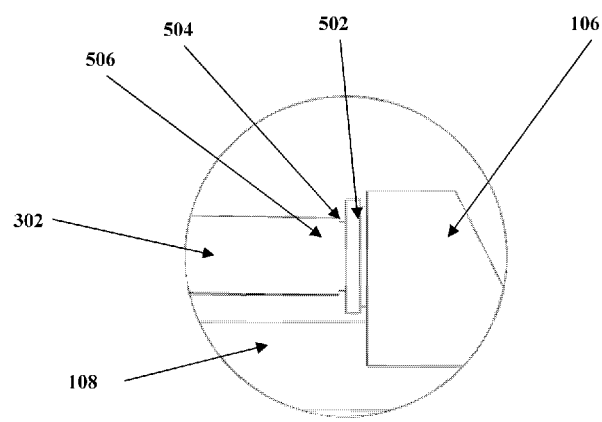
Figure 6:
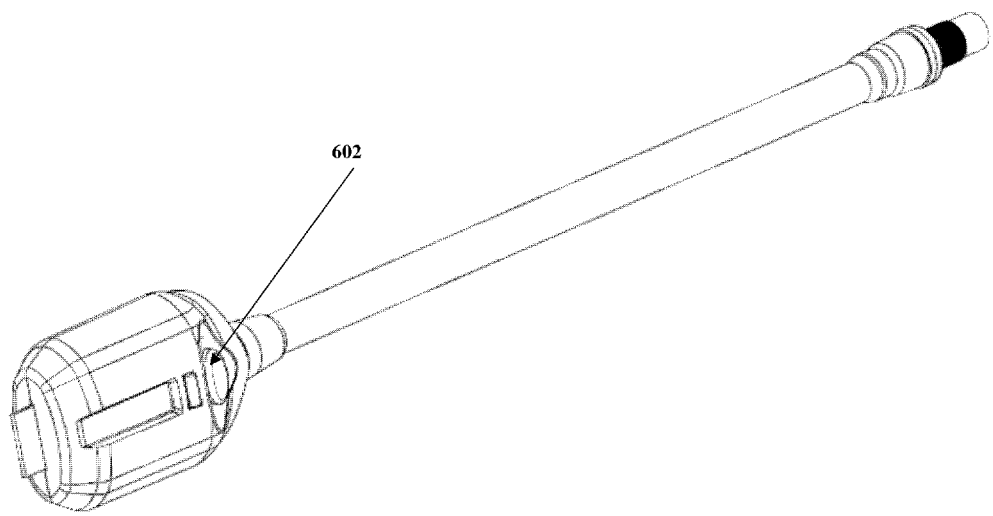

Referring to FIGS. 1-6 we see an embodiment of a multi-LED light source having two portions, an LED cylindrical housing 100 and a power source 102. Note that the use of the term cylindrical is meant to suggest its longitudinal nature, not necessarily its cross section. Thus the LED cylindrical housing 100 may have a circular, semi-circular, square, octagonal or any other suitable elongated geometrical cross shape that allows for the hosting within it of all or portions of a fiber optic cable 104, fiber optic cable adapter 110, one or more LED support structures 106 and/or an electrical connection structure 108.

In one embodiment, the LED cylindrical housing 100 is designed to be nestled and/or removable from a power source 102 or other suitable power supply. In an alternate embodiment, it is designed to be an integral part of said power source 102, with the LED housing 100 being permanently connected to electrical connection structure 108 through to the LED support structures 106 on which the individual LEDs 502 are mounted.

The above arrangements are very common in the medical field, for among other things it allows for any contamination with any fiber optics cable, fiber optic 104, LED housing 100 or other component to be replaced or sterilized, without disposing or exposing the higher cost power supply 102 to damage. In addition, typically the power supply 102 contains all medical grade AC power supplies, and the LED housing 100 and its interface module 112 has within it safe DC voltage signals. The interface 112 may be removed from the power supply 102 by pressing a mechanical release button 602.

In one embodiment the LEDs housing 100 has a distal end equipped with a fiber optic cable adapter 110 (an interface unit designed to connect optically to a longer fiber optic cable), a fiber optic cable within said housing 100 splitting the fiber optic into two or more fiber bundles 302. Each fiber bundle 302 is routed to an individual LED support structure 306 within the LED housing 100.

Each LED support structure 306 is comprised of mechanical and electrical components capable of supporting, powering and removing heat from one or more LEDs 502 on them. Each fiber bundle 302 is individually guided and mechanically secured by a holder 504 within the LED support structure 106 so that the end 506 of the fiber bundle 302 is securely and permanently held against the light emitting portion 508 of the LED, in such a fashion so that the area of the end of the fiber bundle 506 overlays the light emitting area 508 of the LED. In this fashion light losses are minimized.

Since the LEDs supports 106 are housed within the LED housing 100, but separated from each other by a significant distance (determined by the amount of heat being generated by the particular LED chosen within a design), the heat from the LEDs 502 may be transmitted to the LED support structure 106 and/or the electrical connection structure 108 along its length, transferred to the LED housing 100 and directly emitted to the environment without the need to be otherwise removed from within said housing 100. In one embodiment, the interior cavity of the LED housing 100 is completely sealed against fluid penetration. In an alternate embodiment, it is made resistant to fluids, so that only prolonged immersion results in contamination.

Traditional fiber optic cable construction uses various combinations of plastic, composites and/or metal components, materials suited to transmit the heat to the environment. The above is accomplished without any heat sink, fan, or other external heat transfer structure within the connection structure 108, resulting in passive cooling. Alternate embodiments may use Peltier thermo electric cooling at the base of the LED support structure, and or any other suitable electro thermal heat removal technique.

The LED support structures 106 may be built of any structural material suitable to transfer the heat from the LEDs 502 while they operate. In one embodiment, the structures 106 are soldered or otherwise mechanically attached to an electrical and heat transfer structure 108. Such a structure may be a Printed Circuit Board (PCB). PCBs may be made of solid materials such as FR4. In an alternate embodiment, a flex Circuit or Flex PCB may be used. A flex circuit is a patterned arrangement of printed circuitry and components that utilizes flexible based material with or without flexible coverlay. These flexible electronic assemblies may be fabricated using the same components used for rigid printed circuit boards, but allowing the board to conform to a desired shape (flex) during its application.

In one embodiment, the electrical connection structure 108 is comprised of a combination cable, a connector or an extension of a flex circuit board, so that in an alternate embodiment, the electrical connection structure 108 may be a composite, wherein a flexible PCB is used for the portion of the structure containing the LEDs, and a cable is used for the primary electrical coupling function to the power supply. In this fashion, the LED housing 100 may be located far along the fiber cable, almost at the point of light deliver, with an electrical cable extending from the power supply 102 to the electrical connection structure 108 proximal end of the housing 100.

Note that while the LED support structures 106 are shown on top of the transfer structure 108, in an alternate embodiment, they may be mounted on both sides of the structure 108.

In one embodiment, the LEDs 502 are being used are devoid of any and all lensing on its surface, allowing for a perfect match of the flat surface at the end of the fiber 506 with that on top of the LED active light emitting area. In alternate embodiments, lensing on top of the LED active emitting area 508 might be suitable and conformably matched with the end of the fiber 506.

In one embodiment, each fiber bundles 302 is securely attached to the LED support structure 106 through chemical means applied to the holder 504, including gluing using optical epoxy. In an alternate embodiment, they may be screwed in, compressed fitted, or through any suitable mechanical means.

In one embodiment, the proximal end of the LED structure 100 or of the transfer structure itself 108 will have a connector suitable for interfacing with the power supply 102, or with a removable interface module or plug-in housing 112.

A connector 114 is similarly electrically connected to the electrical portion of the structure 108. The LED signals (Power, Status) are communicated to the power supply 102 via said connector. In alternate embodiments, the connection may be routed using flex circuits, direct cables, insertion connectors, etc.

CONCLUSION

In concluding the detailed description, it should be noted that it would be obvious to those skilled in the art that many variations and modifications can be made to the preferred embodiment without substantially departing from the principles of the present invention. Also, such variations and modifications are intended to be included herein within the scope of the present invention as set forth in the appended claims. Further, in the claims hereafter, the structures, materials, acts and equivalents of all means or step-plus function elements are intended to include any structure, materials or acts for performing their cited functions.

It should be emphasized that the above-described embodiments of the present invention, particularly any "preferred embodiments" are merely possible examples of the implementations, merely set forth for a clear understanding of the principles of the invention. Any variations and modifications may be made to the above-described embodiments of the invention without departing substantially from the spirit of the principles of the invention. All such modifications and variations are intended to be included herein within the scope of the disclosure and present invention and protected by the following claims.

The present invention has been described in sufficient detail with a certain degree of particularity. The utilities thereof are appreciated by those skilled in the art. It is understood to those skilled in the art that the present disclosure of embodiments has been made by way of examples only and that numerous changes in the arrangement and combination of parts may be resorted without departing from the spirit and scope of the invention as claimed. Accordingly, the scope of the present invention is defined by the appended claims rather than the forgoing description of embodiments.

The invention claimed is:

1. A high output light emitting diode (LED) based lighting module, comprising:
  a light fiber cable formed by two or more light fiber bundles;
  an LED cylindrical housing containing a plurality of LED support structures, each said LED support structure sequentially laid along the length of said cylindrical housing and separated by some distance from other LED support structures, with each said LED support structure being thermally and electrically connected to one or more electrical and heat transfer structures laid sequentially along the length of said housing, each said LED support structure mounting one or more LEDs and securely holding a light fiber bundle end directly against the light emitting portion of an LED so that said light fiber bundle end slightly overlaps the active area of said LED, whereupon one or more said light fiber bundles are combined at the distal end of said housing into a single light fiber bundle; and
  said LED cylindrical housing containing a portion of said light fiber cable as well as one or more electrical connectors interfacing to a detachable power source.

2. The lighting module of claim 1 further comprising;
  a removable interface module, said removable interface module having one or more electrical connectors for coupling with said one or more LED cylindrical housing electrical connectors and one or more electrical connectors suitable for coupling with a base station; and
  a power source.

3. The lighting module of claim 1 wherein;
  said electrical and heat transfer structure is comprised of a flex circuit.

4. The lighting module of claim 3 further comprising;
  a removable interface module, said removable interface module having one or more electrical connectors for coupling with said one or more LED cylindrical housing electrical connectors and one or more electrical connectors suitable for coupling with a base station; and
  a power source.

\* \* \* \* \*